(12) United States Patent
Huiku

(10) Patent No.: US 6,501,974 B2
(45) Date of Patent: Dec. 31, 2002

(54) COMPENSATION OF HUMAN VARIABILITY IN PULSE OXIMETRY

(75) Inventor: Matti Huiku, Espoo (FI)

(73) Assignee: Datex-Ohmeda, Inc., Madison, WI (US)

( * ) Notice: Subject to any disclaimer, the term of this patent is extended or adjusted under 35 U.S.C. 154(b) by 3 days.

(21) Appl. No.: 09/767,052

(22) Filed: Jan. 22, 2001

(65) Prior Publication Data

US 2002/0133068 A1 Sep. 19, 2002

(51) Int. Cl.[7] .................................................. A61B 5/00
(52) U.S. Cl. ....................... 600/331; 600/310; 600/322; 600/323; 250/252.1
(58) Field of Search ............................... 600/331, 310, 600/321, 322, 323; 250/252.1

(56) References Cited

U.S. PATENT DOCUMENTS

| | | | |
|---|---|---|---|
| 4,086,915 A | 5/1978 | Kofsky et al. ................. 128/2 |
| 4,933,614 A | 6/1990 | Kawata ....................... 318/432 |
| 5,278,627 A | * 1/1994 | Aoyagi et al. ................ 356/41 |
| 5,355,880 A | 10/1994 | Thomas et al. .............. 128/633 |
| 5,357,953 A | * 10/1994 | Merrick et al. .............. 128/633 |
| 5,499,627 A | 3/1996 | Steuer et al. ................ 128/633 |
| 5,630,413 A | 5/1997 | Thomas et al. .............. 128/633 |
| 5,692,503 A | * 12/1997 | Kuenstner ................... 128/633 |
| 5,792,050 A | 8/1998 | Alam et al. .................. 600/310 |
| 5,842,979 A | 12/1998 | Jarman ....................... 600/322 |
| 5,891,024 A | 4/1999 | Jarman et al. ............... 600/323 |
| 5,931,779 A | * 8/1999 | Arakaki et al. .............. 600/310 |
| 6,061,581 A | 5/2000 | Alam et al. .................. 600/310 |
| 6,073,037 A | 6/2000 | Alam et al. .................. 600/310 |
| 6,104,938 A | 8/2000 | Huiku et al. ................. 600/322 |
| 6,163,715 A | 12/2000 | Larsen et al. ................ 600/323 |

FOREIGN PATENT DOCUMENTS

WO    WO 01/03577 A1    1/2001    ............ A61B/5/00

OTHER PUBLICATIONS

International Search Report (3 Pages).

* cited by examiner

Primary Examiner—Henry C. Yuen
Assistant Examiner—Frederick C. Nicolas
(74) Attorney, Agent, or Firm—Marsh Fischmann & Breyfogle LLP

(57) ABSTRACT

The invention relates to the calibration of a pulse oximeter intended for non-invasively determining the amount of at least two light absorbing substances in the blood of a subject. In order to take human variability into account, the calibration is based on an invariant which is a quotient of two pseudo-isobestic signals. Each pseudo-isobestic signal is a weighted sum of two signals, and the weighted sum is theoretically independent of the relative concentrations of said substances in the blood of the subject. By using theoretical values of the invariant on the one hand, and values based on in-vivo measurements on the other hand, the calibration curve of the pulse oximeter is adapted to the characteristics of each individual patient.

16 Claims, 5 Drawing Sheets

COMPENSATION OF HUMAN VARIABILITY IN PULSE OXIMETRY

FIELD OF THE INVENTION

The invention relates generally to pulse oximeters used to detect blood oxygenation. More specifically, the invention relates to a method for calibrating a pulse oximeter and to a pulse oximeter capable of calibrating. The invention further relates to a sensor allowing the calibration of a pulse oximeter, the sensor being an integral part of the pulse oximeter.

BACKGROUND OF THE INVENTION

Pulse oximetry is at present the standard of care for continuous monitoring of arterial oxygen saturation ($SpO_2$). Pulse oximeters provide instantaneous in-vivo measurements of arterial oxygenation, and thereby an early warning of arterial hypoxemia, for example.

A pulse oximeter comprises a computerized measuring unit and a probe attached to the patient, typically to his or her finger or ear lobe. The probe includes a light source for sending an optical signal through the tissue and a photo detector for receiving the signal after transmission through the tissue. On the basis of the transmitted and received signals, light absorption by the tissue can be determined. During each cardiac cycle, light absorption by the tissue varies cyclically. During the diastolic phase, absorption is caused by venous blood, tissue, bone, and pigments, whereas during the systolic phase there is an increase in absorption, which is caused by the influx of arterial blood into the tissue. Pulse oximeters focus the measurement on this arterial blood portion by determining the difference between the peak absorption during the systolic phase and the constant absorption during the diastolic phase. Pulse oximetry is thus based on the assumption that the pulsatile component of the absorption is due to arterial blood only.

Light transmission through an ideal absorbing sample is determined by the known Lambert-Beer equation as follows:

$$I_{out}=I_{in}e^{-\epsilon DC}, \tag{1}$$

where $I_{in}$ is the light intensity entering the sample, $I_{out}$ is the light intensity received from the sample, D is the path length through the sample, $\epsilon$ is the extinction coefficient of the analyte in the sample at a specific wavelength, and C is the concentration of the analyte. When $I_{in}$, D, and $\epsilon$ are known, and $I_{out}$ is measured, the concentration C can be calculated.

In pulse oximetry, in order to distinguish between two species of hemoglobin, oxyhemoglobin ($HbO_2$), and deoxyhemoglobin (RHb), absorption must be measured at two different wavelengths, i.e. the probe includes two different light emitting diodes (LEDs). The wavelength values widely used are 660 nm (red) and 940 nm (infrared), since the said two species of hemoglobin have substantially different absorption values at these wavelengths. Each LED is illuminated in turn at a frequency which is typically several hundred Hz.

The accuracy of a pulse oximeter is affected by several factors. This is discussed briefly in the following.

Firstly, the dyshemoglobins which do not participate in oxygen transport, i.e. methemoglobin (MetHb) and carboxyhemoglobin (CoHb), absorb light at the wavelengths used in the measurement. Pulse oximeters are set up to measure oxygen saturation on the assumption that the patient's blood composition is the same as that of a healthy, non-smoking individual. Therefore, if these species of hemoglobin are present in higher concentrations than normal, a pulse oximeter may display erroneous data.

Secondly, intravenous dyes used for diagnostic purposes may cause considerable deviation in pulse oximeter readings. However, the effect of these dyes is short-lived since the liver purifies blood efficiently.

Thirdly, coatings like nail polish may in practice impair the accuracy of a pulse oximeter, even though the absorption caused by them is constant, not pulsatile, and thus in theory it should not have an effect on the accuracy.

Fourthly, the optical signal may be degraded by both noise and motion artifacts. One source of noise is the ambient light received by the photodetector. Many solutions have been devised with the aim of minimizing or eliminating the effect on the signal of the movement of the patient, and the ability of a pulse oximeter to function correctly in the presence of patient motion depends on the design of the pulse oximeter. One way of canceling out the motion artefact is to use an extra wavelength for this purpose.

A further factor affecting the accuracy of a pulse oximeter is the method used to calibrate the pulse oximeter. Usually the calibration is based on extensive empirical studies in which an average calibration curve is determined based on a high number of persons. By means of this calibration curve, which relates the oxygen saturation of blood to pulse oximeter signals, the average difference between the theory and practice (i.e. in-vivo measurements) is taken into account. The calibration curve typically maps the measured in-vivo signal to a corresponding $SPO_2$ value.

Pulse oximeters, however, can also utilize the Lambert-Beer model for calculating the concentrations of the different Hb species. In this method of calibration, the measurement signals must first be transformed into signals applicable to the Lambert-Beer model for calculation. This transformation constitutes the calibration of the pulse oximeter, since it is the step by means of which the in-vivo signals are adapted into the Lambert-Beer theory according to which the pulse oximeter is designed to operate. Thus, the calibration curves can also be in the form of transformations used to adapt the actual in-vivo measurements to the Lambert-Beer model. Transformations are discussed for example in U.S. Pat. No. 6,104,938.

However, each patient has a calibration curve of his or her own, which deviates from the average calibration curve calculated on the basis of a high number of patients. This is due to the fact that the characteristics of the finger of each patient, such as the absolute amount of venous blood, deviates from those of the average finger. One drawback of the current pulse oximeters is that they are incapable of taking this human variability into account. Human variability here refers to any and all factors causing patient-specific variation in the calibration curve, including time-dependent changes in the calibration curve of a single patient. As discussed in the above-mentioned U.S. Patent, patient-dependent variation can also be seen as an effect of a third substance, such as a third hemoglobin species, in the blood. However, in this context all variation is interpreted as a patient-dependent change in the calibration curve of the pulse oximeter.

It is an objective of the invention to bring about a solution by means of which the patient-specific differences can be taken into account when a pulse oximeter is calibrated. In other words, it is an object of the present invention to create a pulse oximeter which can compensate for the differences in an individual patient as compared to the average calibration or transformation curve which the current pulse oximeter relies on.

A further objective of the invention is to bring about a general-purpose solution for the calibration of pulse oximeters, a solution which is not limited to pulse oximeters explicitly using the transformations as calibration, but which can be applied to any pulse oximeter regardless of its current built-in calibration method.

SUMMARY OF THE INVENTION

These and other objectives of the invention are accomplished in accordance with the principles of the present invention by providing a mechanism by means of which a pulse oximeter can deduce, in connection with each measurement, the patient-specific deviation from an average calibration curve known to the pulse oximeter. Utilizing this difference the pulse oximeter can then determine a new, patient-specific calibration, which takes into account the individual differences to the average calibration curves. The pulse oximeter can thus adapt the calibration to the characteristics of each individual patient.

In its basic embodiment the pulse oximeter comprises three wavelengths. Two of the wavelengths are used for measuring the basic Hb species, i.e. oxyhemoglobin and deoxyhemoglobin, whereas the third wavelength is needed for the calibration method according to the invention.

In the method of the invention, so-called invariants are determined, which are parameters theoretically independent of any tissue or blood parameters, except the known extinction values. The patient-specific variation in these invariants is then used to calibrate the pulse oximeter. A theoretical value is first determined for each invariant on the basis of the average calibration curve, and then in a similar way a second value is further determined for the same invariants, except that the measured (in-vivo) signals are used instead of theoretical measurement signals. Each second value is then compared to the corresponding theoretical value and the difference(s) is/are used for calibration purposes.

The method is not limited to pulse oximeters explicitly using the transformations, but can be applied to any pulse oximeters. However, the way the above-mentioned difference(s) in the values of the invariant is/are used for calibration purposes depends on the type of the pulse oximeter. In a transformation-based pulse oximeter, a new patient-specific transformation can be searched for on the basis of the difference, the new transformation being such that it yields a minimum difference between said theoretical value and a second value determined on the basis of the new transformation itself. In a conventional pulse oximeter, which maps the measurement signal to arterial oxygen saturation, the above-mentioned difference in the values of the invariant can be mapped to an error value indicating a patient-specific divergence from an average value for arterial oxygen saturation.

BRIEF DESCRIPTION OF THE DRAWINGS

In the following, the invention and its preferred embodiments are described more closely by referring to the examples shown in FIGS. 1 to 7 in the appended drawings, wherein.

DETAILED DESCRIPTION OF THE INVENTION

Below, the solution according to the invention is first discussed with reference to the basic embodiment of a pulse oximeter according to the invention, i.e. a pulse oximeter with a minimum number of wavelengths. This kind of a pulse oximeter utilizes three wavelengths: two of the three wavelengths being required for measuring the above-mentioned two species of hemoglobin, oxyhemoglobin, and deoxyhemoglobin, the third wavelength being for the self-calibration method according to the invention. Moreover, it is first assumed that the pulse oximeter utilizes transformations, since in these pulse oximeters the human variability can be addressed in a sophisticated way. As mentioned above, U.S. Pat. No. 6,104,938 discloses a pulse oximeter of this type.

Figure 1:
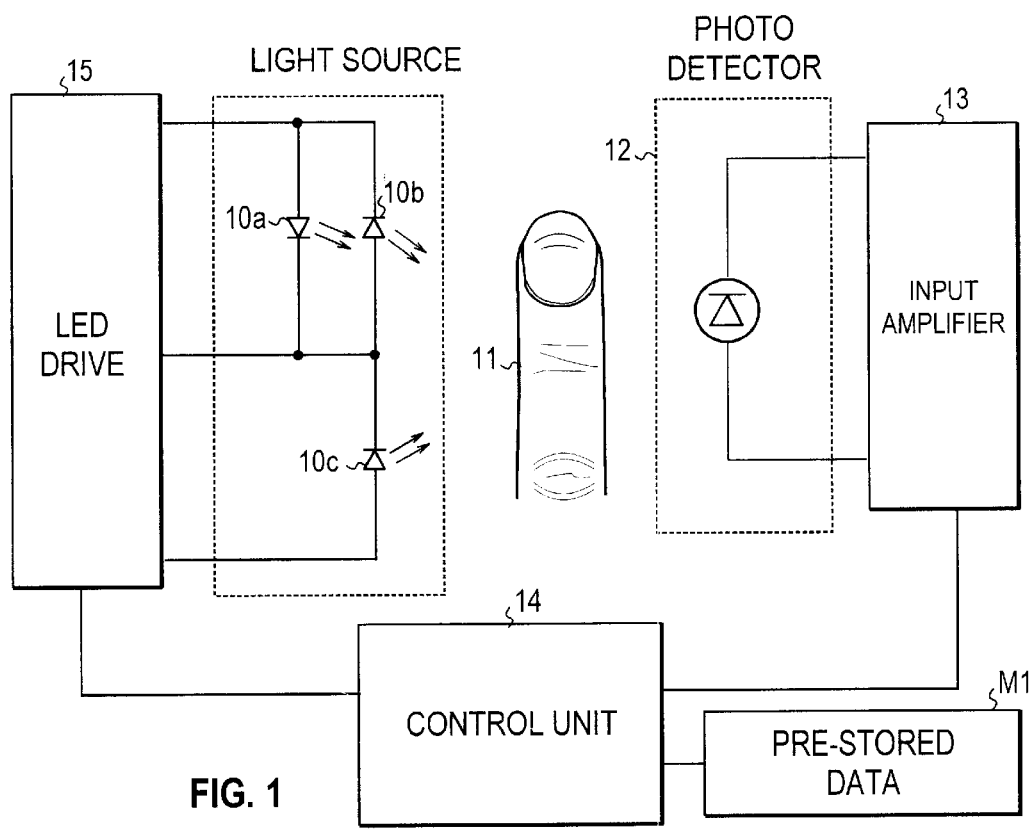
FIG. 1 illustrates the basic embodiment of a pulse oximeter according to the present invention.

FIG. 1 is a block diagram of the basic embodiment of a pulse oximeter according to the present invention. Light from three different LEDs 10a, 10b and 10c, each operating at a respective wavelength, passes into patient tissue, such as a finger 11. The light propagated through or reflected from the tissue is received by a photodetector 12, which converts the optical signal received into an electrical signal and feeds it to an input amplifier 13. The amplified signal is then supplied to a control unit 14, which carries out inter alia the calibration method according to the invention. The control unit further controls the LED drive 15 to alternately activate the LEDs. As mentioned above, each LED is typically illuminated several hundred times in a second.

Figure 2:
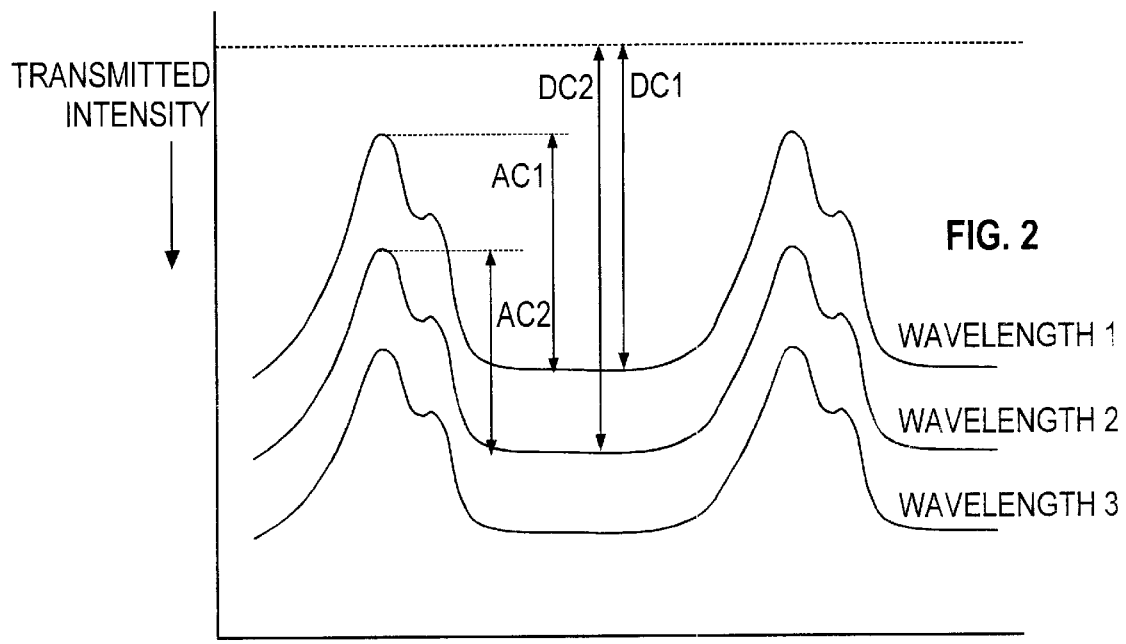
FIG. 2 illustrates the signals utilized in the pulse oximeter of FIG. 1.

When each LED is illuminated at such a high rate as compared to the pulse rate of the patient, the control unit obtains a high number of samples at each wavelength for each cardiac cycle of the patient. The value of these samples (i.e. the amplitude of the received signal) varies according to the cardiac cycle of the patient, the variation being caused by the arterial blood, as mentioned above. The control unit therefore utilizes three measurement signals, as shown in FIG. 2, each being received at one of the wavelengths.

In order for variations in extrinsic factors, such as the brightness of the LEDs, sensitivity of the sensors, or thickness of the finger, to have no effect on the measurement, each signal received is normalized by extracting the AC component oscillating at the cardiac rhythm of the patient, and then dividing the AC component by the DC component of the light transmission or reflection. The signal thus obtained is independent of the above-mentioned extrinsic factors. Thus the control unit utilizes three normalized signals, which are in the following denoted with $$dA_i = \frac{AC_i}{DC_i},$$

where i is the wavelength in question (in this basic embodiment of the pulse oximeter i=1,2,3), $AC_i$ is the AC component at wavelength i, and $DC_i$ is the DC component at wavelength i. The signals are also referred to below as modulation signals. The modulation signals thus indicate how absorption is affected by the arterial blood of the patient.

The above-described measurement arrangement corresponds to a conventional three-wavelength pulse oximeter. The method of the present invention is implemented in the control unit of the pulse oximeter on the basis of the three modulation signals described above, i.e. the novelty of the system resides within the control unit itself. However, to be able to perform the self-calibration in conjunction with each patient, the control unit requires some pre-calculated data, which is stored in the memory (M1) of the pulse oximeter. Instead of being stored in conjunction with the control unit, this data, or at least part of it, can also be stored in the sensor part of, the pulse oximeter. The sensor part, including at least the LEDs and the photo detector, is connected to the signal processing part, which includes the control unit. Consequently, depending on the overall configuration, the novelty can also reside partly in the sensor. The operation of the pulse oximeter is discussed in more detail below.

The theory of pulse oximetry is generally presented as being based on the Lambert-Beer Law. According to this theory, light transmission through the tissue at each wavelength is exponentially dependent on the absorbance of the tissue (equation 1). This theory is generally accepted and established in pulse oximetry.

Next to be discussed is the theory and formalism on which the method of the invention is based.

According to the Lambert-Beer theory, the signals described above can be presented as follows:

$$dA_1 = dA \times (\epsilon_1^{HbO_2} \times HbO_2 + \epsilon_1^{RHb} \times RHb)$$

$$dA_2 = dA \times (\epsilon_2^{HbO_2} \times HbO_2 + \epsilon_2^{RHb} \times RHb)$$

$$dA_3 = dA \times (\epsilon_3^{HbO_2} \times HbO_2 + \epsilon_3^{RHb} \times RHb)$$

$$RHb = 1 - HbO_2$$

where dA is a common factor which depends on the absolute values, i.e. on the total amount of hemoglobin, $\epsilon_i^{HbO_2}$ is the extinction coefficient of oxyhemoglobin at wavelength i (i=1,2,3), $\epsilon_i^{RHb}$ is the extinction coefficient of deoxyhemoglobin at wavelength i, $HbO_2$ is the concentration of oxyhemoglobin, and RHb is the concentration of deoxyhemoglobin.

Figure 3:
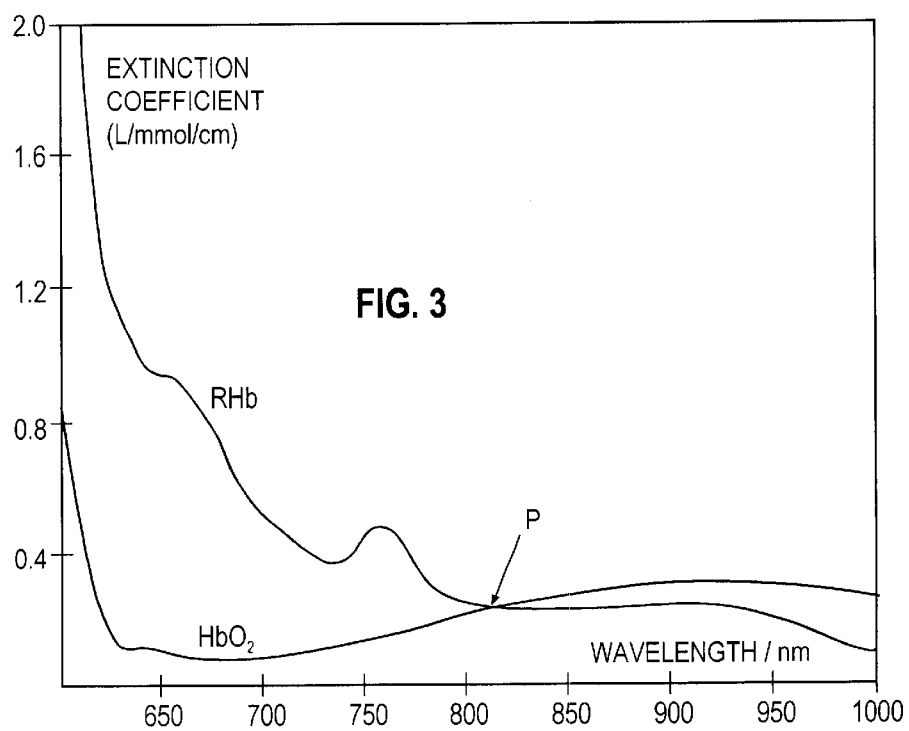
FIG. 3 shows the extinction coefficients of two different species of hemoglobin as a function of wavelength.

FIG. 3 shows the extinction coefficients ($\epsilon^{HbO_2}$ and $\epsilon^{RHb}$) of oxyhemoglobin ($HbO_2$) and deoxyhemoglobin (RHb) as a function of the wavelength. The uniqueness of the present invention begins with the isobestic point present in the extinction coefficient curve. Traditionally, the isobestic point is at the wavelength where the extinction curves of the particular hemoglobin species cross. In other words, point P in the figure is the isobestic point of oxyhemoglobin ($HbO_2$) and deoxyhemoglobin (RHb). The point has the special property that the modulation signal at the wavelength in question does not depend on the respective proportions (relative concentrations) of the hemoglobin species. Thus at the wavelength of point P the effect of the relative concentrations of oxyhemoglobin and deoxyhemoglobin on the result of the measurement is nil. It should be noted, however, that the modulation signal is independent of the relative concentrations only, not of the absolute concentrations. Thus, the absolute amount of the hemoglobin species has an effect on the result of the measurement.

In order to make the modulation signals utilized in the pulse oximeter according to the invention independent of the relative concentrations of the two hemoglobin species, a weighted sum of two modulation signals is utilized in the calibration process, the weight being selected so that the sum signal is isobestic. This sum signal is in this context called a pseudo-isobestic (PI) signal and is denoted by $S_{i,j}^{PI}$, where i and j are the wavelengths. Thus, a pseudo-isobestic signal is here defined as a signal calculated from the signals at two different wavelengths by summing the signals with a particular weight. The corresponding wavelengths are pseudo-isobestic within this weight. The pseudo-isobestic signal calculated from the signals at wavelengths 1 and 2, for example, is thus:

$$S_{1,2}^{PI} = dA_1 f_{1,2} \times dA_2$$

where $f_{1,2}$ is the said weight. If $S_{1,2}^{PI}$ does not depend on the oxyhemoglobin fraction $HbO_2$ ($RHb = 1 - HbO_2$), i.e. if $$\frac{\partial}{\partial (HbO_2)} S_{1,2}^{PI} = 0,$$

we get:

$$f_{1,2} = \frac{\epsilon_1^{HbO_2} - \epsilon_1^{RHb}}{\epsilon_2^{HbO_2} - \epsilon_2^{RHb}}.$$

Taking into account the above equations of the modulation signals, the pseudo-isobestic signal calculated from the signals at wavelengths 1 and 2 can be written as follows:

$$S_{1,2}^{PI} = dA \times (\epsilon_1^{RHb} = f_{1,2} \times \epsilon_2^{RHb}) \qquad (2)$$

Thus, the pseudo-isobestic signal is still dependent on the total volumes of oxyhemoglobin and deoxyhemoglobin, since dA is dependent on said total volumes. Therefore, the signals are further normalized by forming a quotient of two pseudo-isobestic signals. The resulting parameter is in this context termed "pseudo-isobestic invariant" (PII), since it is, theoretically, a constant parameter (i.e. an invariant). The pseudo-isobestic invariant is thus defined as follows:

$$PII_{i,j,k,l} = \frac{S_{i,j}^{PI}}{S_{k,l}^{PI}}, \qquad (2a)$$

where i,j,k, and I represent the wavelengths.

As is obvious from the above equations, the pseudo-isobestic invariant is, according to the Lambert-Beer theory, independent of any tissue or blood parameters, except the extinction values, which are known. Therefore, if the pseudo-isobestic invariant diverges from its theoretical value, the divergence must be caused by the variability between two individual patients or by temporal variations in the measurement conditions of a single patient. In other words, the divergence is caused by human variability. The pseudo-isobestic invariant can therefore be used for compensating the patient-specific variations in the calibration curve. This use of the PII is discussed in the following.

As is known, there is a difference between the Lambert-Beer theory and the practical measurements. The difference is due to the fact that the Lambert-Beer theory does not take into account the scattering and non-homogeneity of the tissue, whereas the actual extinction coefficients are also dependent on the scattering of light caused by the tissue and blood, and on the combined effect of absorption and scattering. The larger the proportion of the attenuation caused by absorption and scattering, the larger is the correction needed between the actual and the theoretical domains. This correction between these two domains can be represented by the above-discussed transformation curves, by means of which the actual in-vivo measurements are mapped to the Lambert-Beer model. The transformation is discussed in more detail in the above-mentioned U.S. Pat. No. 6,104,938.

Figure 4A:
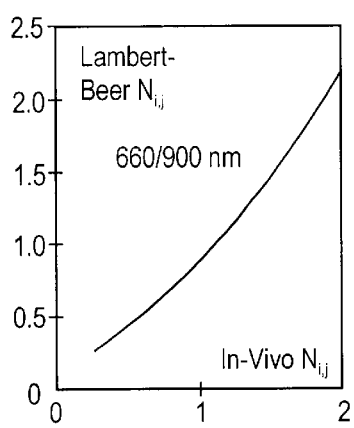
FIGS. 4a to 4f illustrate the average transformation curves for two different pulse oximeters.
Figure 4B:
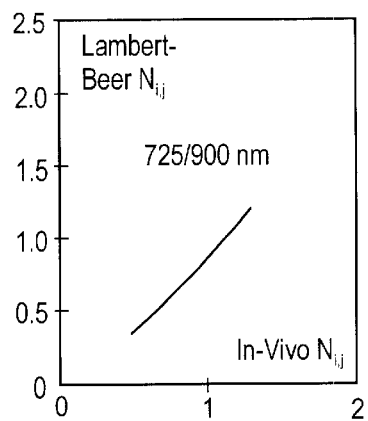
Figure 4C:
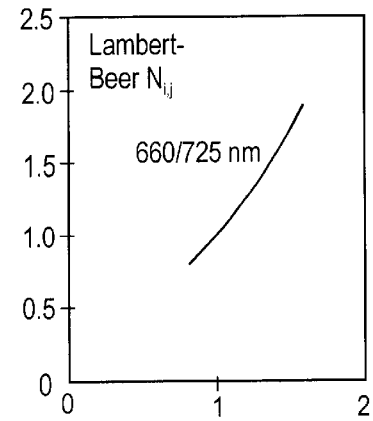
Figure 4D:
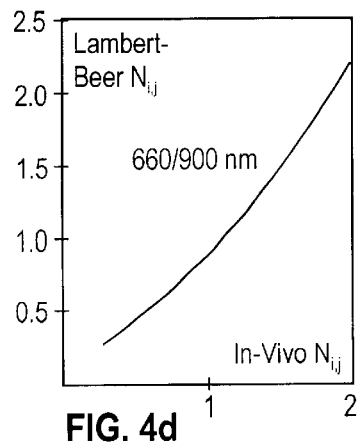
Figure 4E:
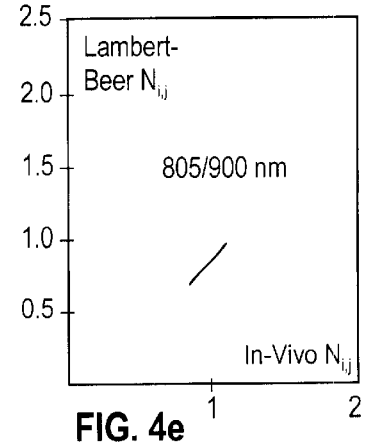
Figure 4F:
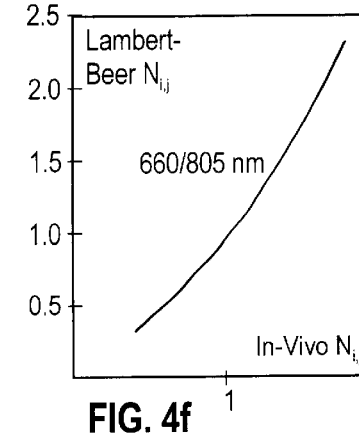

The transformation can be expressed, for example, as follows:

$$N_{k,l}{}^{LB} = g^{k,l}(N_{k,l}{}^{in\text{-}vivo}) \tag{3}$$

where $$N_{k,l} = \frac{dA_k}{dA_l}$$

is the modulation ratio (the superscript indicating the domain), g is the transformation, in the form of a polynomial function (the superscript indicating the wavelengths in question), for example, and k and l are the wavelengths FIGS. 4a to 4f illustrate the average transformation curves measured for a pulse oximeter, where the two wavelengths for measuring the two species of hemoglobin are 660 nm and 900 nm and the third wavelength used for the self-calibration method according to the invention is either 725 nm or 805 nm. FIGS. 4a to 4c illustrate the transformation curves for a pulse oximeter with the third wavelength being 725 nm, and FIGS. 4d to 4f illustrate the transformation curves for a pulse oximeter with the third wavelength being 805 nm. Each curve shows the Lambert-Beer $N_{k,l}$ as a function of the in-vivo $N_{k,l}$ at wavelengths k and l.

There are two basic ways to determine the average transformation, a theoretical approach and an empirical approach. In the empirical approach the measurements are made in the tissue by taking blood samples and measuring the actual proportions of the hemoglobin species and then determining the value of $N_{k,l}$ on the basis of the measured proportions. The transformation is then obtained as the relationship between the values based on the blood samples and the values given by empirical measurements as measured by the pulse oximeter. The theoretical approach, in turn, is based on a known tissue model which takes into account the above-referred characteristics of the tissue which are ignored in the Lambert-Beer model. A first value is determined for in-vivo $N_{k,l}$ by means of the tissue model and a second value on the basis of the Lambert-Beer model. Thus in the theoretical approach no empirical measurements are made.

In practice the transformation can be a quadratic equation which causes a correction of the order of 20 percent to the measured $N_{k,l}$ value, for example. As discussed below, the transformation data (i.e. the transformation curves) are preferably stored in the pulse oximeter, or in the sensor, in numeric form. The number of transformation curves stored in the pulse oximeter can vary, depending on the number of wavelengths used, for example. Typically there is a transformation curve for each wavelength pair.

The relationship between the pseudo-isobestic invariant PII and the transformation g can then be presented by the equation:

$$PII_{i,j,k,l} = \frac{S_{i,j}^{PI}}{S_{k,l}^{PI}} = \frac{dA_i + f_{i,j} \times dA_j}{dA_k + f_{k,l} \times dA_l} = \frac{dA_j}{dA_l} \times \frac{\frac{dA_i}{dA_j} + f_{i,j}}{\frac{dA_k}{dA_l} + f_{k,l}} \tag{4}$$

$$= N_{j,l}^{LB} \times \frac{N_{i,j}^{LB} + f_{i,j}}{N_{k,l}^{LB} + f_{k,l}} = g^{j,l}\left(N_{j,l}^{in\text{-}vivo}\right) \times \frac{g^{i,j} N_{i,j}^{in\text{-}vivo} + f_{i,j}}{g^{k,l} N_{k,l}^{in\text{-}vivo} + f_{k,l}}$$

According to the invention, the above-described formalism, i.e. the pseudo-isobestic invariants (PIIs) are used to compensate for the human variability present in the pulse oximeter measurements.

The effect of human variability can be seen, for example, so that it changes the transformation curves from the in-vivo $N_{k,l}$ values to the Lambert-Beer $N_{k,l}$ values (cf. FIGS. 4a to 4f). The compensation is based on the calculation in the first phase of a theoretical value for the pseudo-isobestic invariant according to the Lambert-Beer theory, and then the calculation of a second value for the same pseudo-isobestic invariant in the second phase according to the measured signals, using the average transformation curves for mapping the measured signals in the Lambert-Beer model so that said second value can be calculated (Equation 4). The value of the pseudo-isobestic invariant obtained in the second phase is then compared to the theoretical value obtained in the first phase. If a difference is detected, a new calibration is sought based on the magnitude of the difference.

When the pulse oximeter is a type utilizing the above-described transformations, a new transformation is sought, the new transformation being such that when it is used for mapping the measured signals in the Lambert-Beer model, the resulting value of the invariant equals, as accurately as possible, the theoretical value calculated in the first phase. The approximate average transformation can then be replaced by a more accurate transformation that takes the human variability into account. Thus the patient-specific change in the transformation is seen as a change in the value of the pseudo-isobestic invariant calculated from the in-vivo signals.

Figure 5:
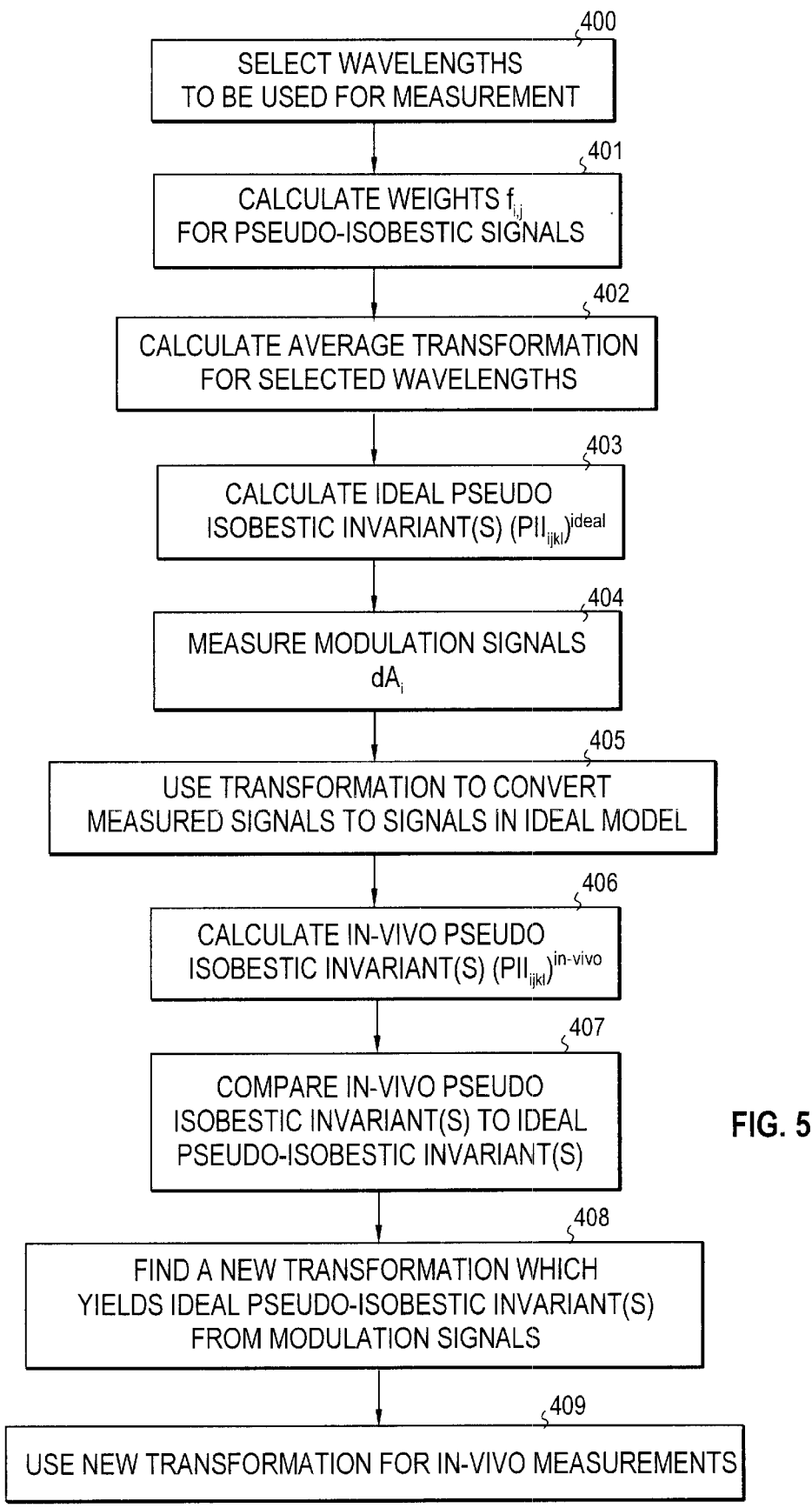
FIG. 5 is a flow diagram illustrating the first embodiment of the calibration method of the invention.

FIG. 5 is a flow diagram illustrating the steps of the calibration method according to the invention, assuming that the pulse oximeter uses the transformations for calibration purposes. In the figure, it is still assumed that the calibration is performed for a three-wavelength pulse oximeter described above.

The first four steps (400 to 403) shown in the figure are performed in advance, i.e. before the actual in-vivo measurement is performed at step 404. These first four steps can be performed during the manufacturing phase of the pulse oximeter in the factory.

First, the wavelengths to be used are selected for the measurement (step 400). As mentioned above, it is assumed here that three wavelengths are selected at this step. The wavelengths can be those discussed in connection with FIGS. 4a to 4f, for example.

When the wavelengths have been selected, the weights f are calculated for "ideal" pseudo-isobestic signals. It is to be noted here that the weights can be calculated already in this phase, i.e. before the actual measurements are performed, since the calculation is based on the extinction coefficients of the ideal model shown in FIG. 3, i.e. the said figure belongs to the ideal Lambert-Beer domain and the isobestic point and the pseudo-isobestic signals are present only in the ideal model.

The average transformation curves according to FIGS. 4a to 4f are then determined for the selected wavelengths at step 402. The transformation curves can be determined immediately when the wavelengths are fixed. As discussed above, these transformation curves are used later in the process to convert the actual in-vivo signals to signals that can be applied to the Lambert-Beer model, so that the pseudo-isobestic invariants can be determined again, this time on the basis of the measured signals brought to the Lambert-Beer model by means of said transformation curves.

Next, the "ideal" pseudo-isobestic invariant(s) $(PII_{ijkl})^{ideal}$ (equation 2a) is/are calculated at step 403. When three wavelengths are used, six pseudo-isobestic signals $(S_{1,2}, S_{1,3}, S_{2,1}, S_{2,3}, S_{3,1}, S_{3,2})^{PI}$ can be determined (i.e. two wavelengths out of three can be selected in six different ways) according to equation (2). Further, six different PIIs can be determined. However, only one of the PIIs is independent and provides the basis for calculating the other five.

As mentioned previously, the above steps are performed in the pulse oximeter prior to its use for in-vivo measurements. Said measurements can now be initiated.

When in-vivo measurement is performed in the known manner, the pulse oximeter measures the three modulation signals $dA_i$ (i=1,2,3) (step 404).

The approximate transformation curves calculated earlier at step 403 are then used at step 405 to convert the measured modulation signals into Lambert-Beer signals (equation 3). After this, the in-vivo pseudo-isobestic invariants are calculated on the basis of these signals (step 406). The calculation is performed as described above (equations 3 and 4) and similarly as in the production phase (step 402), the only exception being that now the pseudo-isobestic invariant(s) is/are calculated on the basis of real measurement signals brought to the "ideal" model by means of a transformation, which is correct only for average human tissue.

The in-vivo invariant is then compared (step 407) to the "ideal" invariant obtained at step 403. If the difference between these two is greater than the maximum difference allowed, a new transformation is sought. This new transformation is such that when it is used at step 405 for the same measurement signals, the value of the in-vivo pseudo-isobestic invariant obtained on the basis of this transformation corresponds, as accurately as possible, to the value of the ideal invariant obtained at step 403. In other words, this new transformation takes into account the differences in the current patient as compared to the average transformation curve. The new transformation is thus a tailored transformation for the current patient and can therefore be used for the measurements relating to the current patient. In the above-described manner the pulse oximeter calibrates itself for each patient.

In order for the pulse oximeter to perform the above steps, the pre-calculated data in its memory includes the average transformation curves illustrated in FIGS. 4a to 4f. As mentioned above, these curves can be determined in two basic ways. The memory preferably contains a look-up table including the numeric data constituting the transformation curves.

Figure 6:
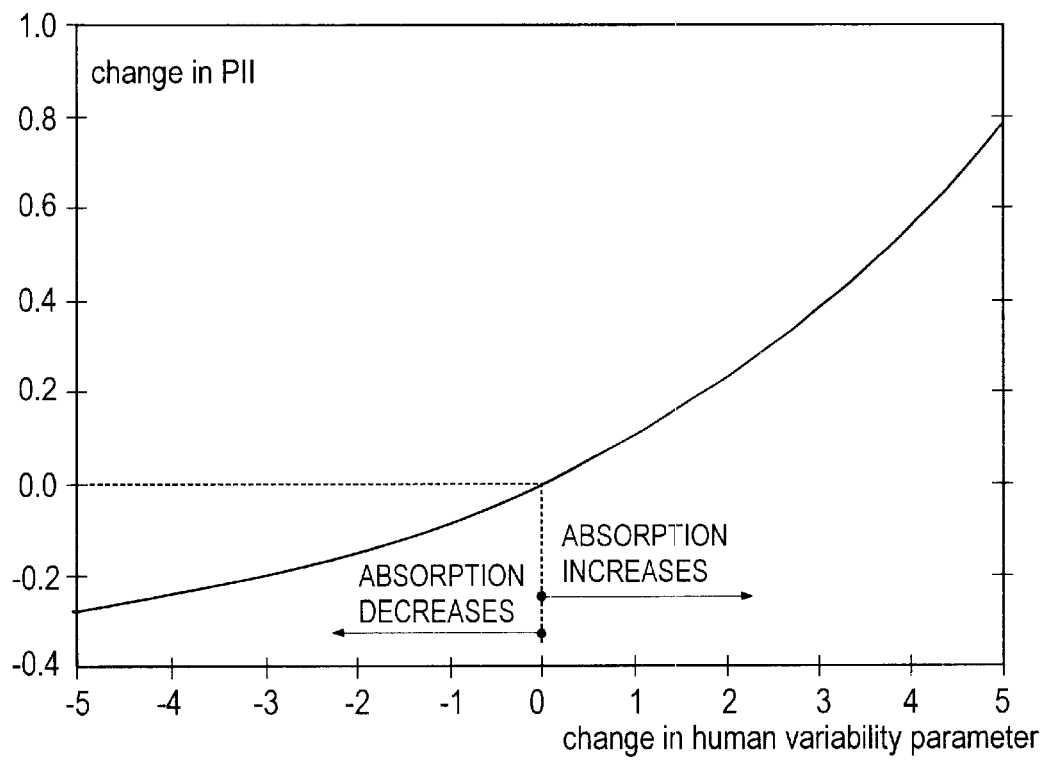
FIG. 6 illustrates the general principle of using the pseudo-isobestic invariants according to the present invention.

The determination of the patient-specific transformation curve(s) can be performed purely on the basis of the difference between the PII values and the above-mentioned transformation curves. The change in the value of PII is caused by a change in one or more physiological factors which cause a change in the absolute absorption. It is possible to determine a curve to indicate how the changes in absorption affect the PII. This curve is illustrated in FIG. 6. As can be seen from the curve, when the absorption increases, the value of PII increases and when absorption decreases, the value of PII decreases. The curve can be constructed either empirically or theoretically using a tissue model.

For calibration purposes, exact knowledge about the physiological factor causing the change is not important, of sole relevance is whether this change causes a change in the transformation curve. Therefore, it is only important to find the change in the transformation curve, i.e. the new transformation curve. This new transformation can be searched for entirely on the basis of the pre-stored transformation curve according to FIGS. 4a to 4f. The search can be performed in an iterative manner by shifting the transformation curve in small steps and calculating the difference from the ideal invariant at each step. Thus, steps 405–407 are repeated for each step. The new transformation is the one that yields the minimum difference between the in-vivo and the ideal value. On the basis of the curve of FIG. 6, the pulse oximeter knows whether the absorption has increased or decreased, and therefore it also knows in which direction the transformation curves must be shifted (i.e. up or down in FIGS. 4a to 4f).

Figure 7:
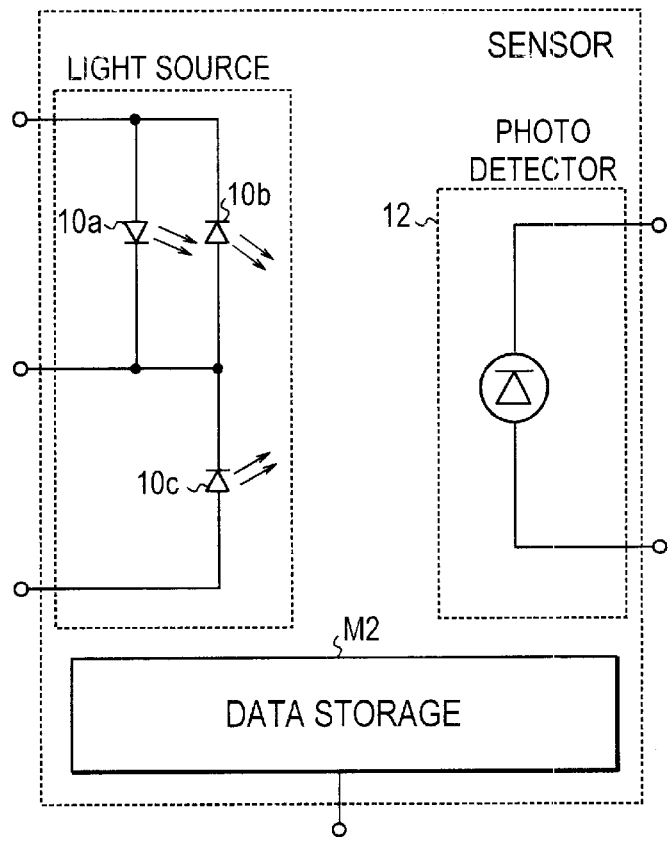
FIG. 7 illustrates the basic structure of a sensor according to the invention.

The pre-calculated data utilized by the pulse oximeter can also be stored in the sensor part of the pulse oximeter, whereby the same sensor can be attached to different pulse oximeter housings. FIG. 7 illustrates the general structure of a sensor according to the invention, the detailed configuration of the sensor being dependent on which information is stored in the sensor and which in the signal processing part, and also on the amount of calculation that is appropriate in the signal processing part.

Nevertheless, a sensor according to the invention includes the light sources (10a, 10b, 10c) and the photo detector (12), the light sources being adapted to emit at three or more wavelengths. In addition, the sensor includes a data storage unit M2 for storing the data on the basis of which the signal processing part can perform the above-described calibration. In one embodiment the data storage unit contains the look-up tables including the average transformation curves and one or more numeric values of the "ideal" pseudo-isobestic invariants $(PII_{ijkl})^{ideal}$. In another embodiment the extinction values can be stored in the sensor instead of the PII values, whereby the PII values are calculated in the signal processing part on the basis of the extinction values obtained from the sensor. In a third embodiment the data storage unit includes data on the wavelengths of the sensor, on the basis of which the numeric PII values can be calculated in the signal processing part of the pulse oximeter. The average transformation curves can also be determined in the apparatus on the basis of the wavelength information if the look-up tables are not stored in the sensor. Thus, in its simplest form the data storage unit includes only data on the wavelengths used, although it typically includes the transformation data according to FIGS. 4a to 4c (or 4d to 4f) and one or more numeric values for the "ideal" pseudo-isobestic invariant.

If more than three wavelengths are used in the pulse oximeter, either the extra wavelengths after the first three can be used entirely for the self-calibration method according to the invention or part or all of the extra wavelengths can be used for measuring additional information, such as methemoglobin (MetHb) and/or carboxyhemoglobin (CoHb).

As is obvious from the above definition, the number of pseudo-isobestic invariants available depends on the number of wavelengths used for the method according to the invention. In the basic embodiment, six PIIs are available, although only one of them is independent, while the others depend on the said independent one. In case of four wavelengths, thirty PIIs can be obtained, although only two of them are independent, while the others depend on the said two. The number of independent PIIs corresponds to N minus 2, if N is the number of wavelengths (provided that all extra wavelengths are used for the method according to the invention).

When several pseudo-isobestic invariants are used, various criteria can be applied for finding the new transformation that yields the minimum difference. One possible method is the least squares method, i.e. the transformation is sought which minimizes the sum, where each factor represents the square of difference between the in-vivo and the ideal values of an individual PII. Weights can also be used to put more weight on desired PIIs.

Figure 8:
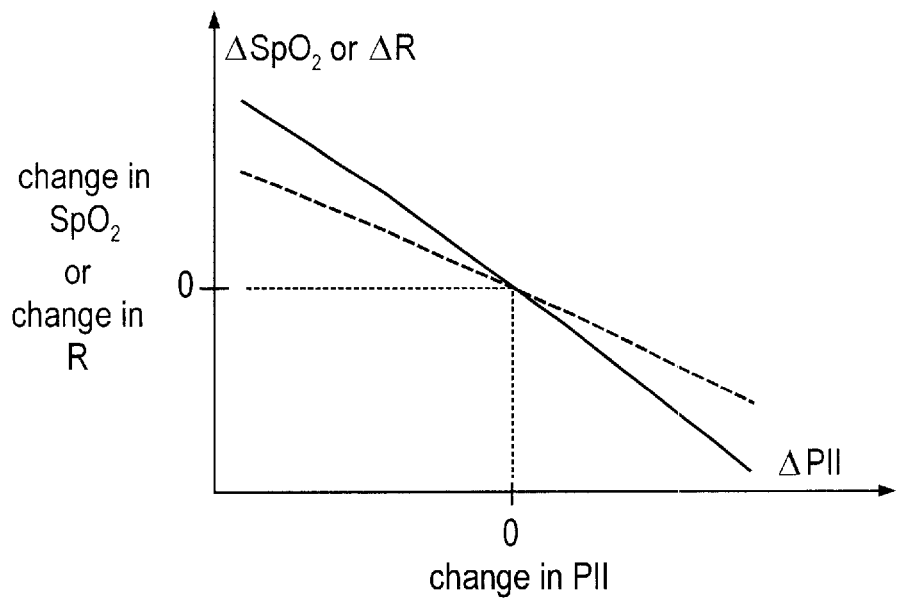
FIG. 8 illustrates the way the method of the invention can be used in conventional pulse oximeters.
Figure 9:
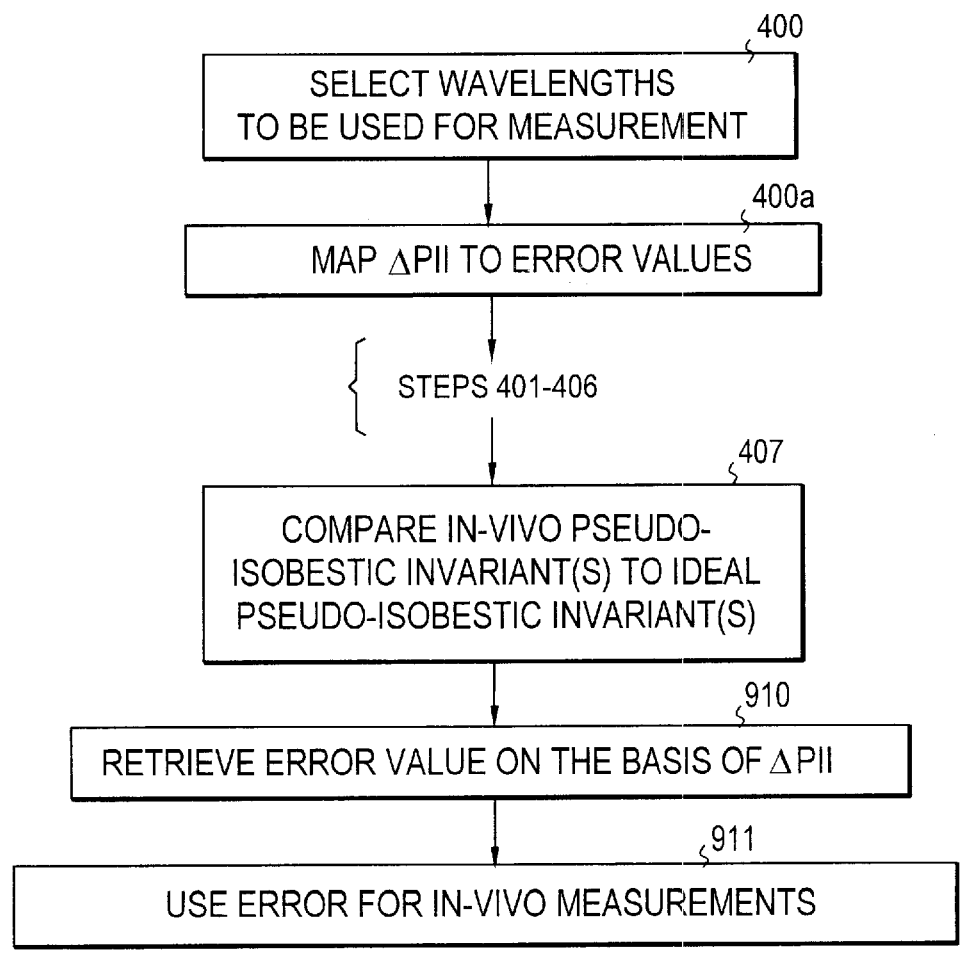
FIG. 9 is a flow diagram illustrating the second embodiment of the calibration method of the invention.

In the above examples, it was assumed that the pulse oximeter explicitly uses the transformations for calibration, whereby the transformation is changed so that patient-specific variation is compensated for. Since in a conventional pulse oximeter the measurement signal is mapped to a $SpO_2$ value, the difference between the in-vivo invariant and the "ideal" invariant can be used to indicate the error in the $SpO_2$ value. This is illustrated in FIG. 8. Thus, in this case no transformation is changed but the said difference is mapped directly to the $SpO_2$ error. As shown in the shortened flow chart of FIG. 9, this second embodiment of the method otherwise includes the same steps as in the above-described first embodiment, except that step 400a has been added and steps 408 and 409 have been replaced by the new steps 910 and 911, respectively. At step 400a, the relationship depicted in FIG. 8 is created, the relationship indicating how said difference in the PII is related to the $SpO_2$ error. As the average transformation, the curve according to FIG. 8 can also be generated empirically by taking blood samples, or theoretically based on a known tissue model. At step 910 the pulse oximeter maps the difference detected at step 407 to the $SpO_2$ error, using the relationship created at step 400a. This error is then used to correct the measured values (step 911).

Correspondingly, the difference between the two values of the PII can be mapped directly to any other quantity by which the pulse oximeter can correct the average calibration known to it in order to take into account the human variability. This quantity can be, for example, the modulation ratio R. In standard pulse oximeters the modulation ratio R is usually related to $SpO_2$ values at the wavelengths of 660 nm and 900 nm. The general form of this relationship is: $SpO_2 = AR^2 + BR + C$, where A, B, and C are constants.

The relationship according to FIG. 8 can be stored in the form of a look-up table, for example, from which the error value corresponding to a given difference can be retrieved.

A further advantage of the pulse oximeter according to the invention is that the pseudo-isobestic signal can also be used as a measure of perfusion. Since the pseudo-isobestic signal $S_{i,j}^{PI}$ is dependent only on variables which change when the perfusion changes, it can be used as a perfusion index. The pulse oximeter of the invention therefore automatically provides a measurement value for patient-specific perfusion. As is obvious from the above, the minimum number of wavelengths for a perfusion index is two.

Although the invention was described above with reference to the examples shown in the appended drawings, it is obvious that the invention is not limited to these, but may be modified by those skilled in the art without departing from the scope and spirit of the invention.

What is claimed is:

1. A method for calibrating an apparatus intended for non-invasively determining an amount of at least two light absorbing substances in the blood of a subject and being provided with emitter means for emitting radiation at a minimum of three different wavelengths, the method comprising the steps of:
    (a) according to the Lambert-Beer model, determining a theoretical measurement signal for each wavelength used in the apparatus,
    (b) according to the Lambert-Beer model, determining an invariant which is a quotient of two pseudo-isobestic signals, each pseudo-isobestic signal being a weighted sum of two measurement signals, the weighted sum being theoretically independent of the relative concentrations of said substances in the blood of the subject,
    (c) calculating a first value for said invariant by means of said theoretical measurement signals,
    (d) performing an in-vivo measurement on a living tissue with the apparatus, whereby in-vivo measurement signals are obtained for each wavelength,
    (e) applying a transformation on said in-vivo measurement signals for transforming said signals to the Lambert-Beer model, whereby transformed in-vivo measurement signals are obtained,
    (f) calculating a second value for said invariant, the second value being calculated similarly to the first value, except for the replacement of said theoretical measurement signals by the transformed in-vivo measurement signals,
    (g) comparing the second value with the first value of the invariant, and
    (h) calibrating the apparatus on the basis of a difference between said first value and said second value.

2. A method according to claim 1, wherein step (h) includes:
    determining a new transformation which is such that a value calculated for said invariant as the first value, except for the replacement of said theoretical measurement signals by transformed in-vivo signals obtained by applying the new transformation, corresponds to the first value with a sufficient accuracy, and
    calibrating the apparatus based on the new transformation.

3. A method according to claim 1, wherein step (h) includes:
    mapping said difference to an error value indicating a divergence from a specified value of a given quantity, and
    calibrating the apparatus based on the error value.

4. A method according to claim 2, further comprising the step of storing in the apparatus numeric data representing the transformation.

5. A method according to claim 4, wherein the new transformation is determined iteratively by means of said numeric data.

6. A method according to claim 4, further comprising the step of storing the first value of the invariant permanently in the apparatus.

7. A method according to claim 6, wherein steps (a) to (c) are performed in the manufacturing phase of the apparatus and steps (e) to (h) for each in-vivo measurement according to step (d).

8. An apparatus for non-invasively determining an amount of at least two light absorbing substances in the blood of a subject, the apparatus comprising:
    emitter means for emitting radiation at a minimum of three different wavelengths,
    detector means for receiving said radiation at each of said wavelengths and producing at least three electrical output signals,
    signal processing means for processing said output signals and producing a modulation signal for each wavelength, each modulation signal representing pulsating absorption caused by arterialized blood of the subject, transformation means for applying a transformation on each said modulation signal, whereby transformed modulation signals applicable in the Lambert-Beer model are obtained, calculation means, responsive to said transformation means, for determining a value for an invariant on the basis of the transformed modulation signals, the invariant being in the Lambert-Beer model a quotient of two pseudo-isobestic signals, each pseudo-isobestic signal being a weighted sum of two transformed modulation signals, the weighted sum being independent of the relative concentrations of the substances, and determining means for specifying a transformation whose application on said modulation signals yields a value for the invariant which meets a predetermined criterion.

9. An apparatus according to claim 8, wherein the determining means are adapted to specify a transformation whose application on said modulation signals yields a value which equals a predetermined value with a given accuracy.

10. An apparatus according to claim 8, wherein the transformation means include a set of transformation curves stored in numeric format.

11. An apparatus for non-invasively determining an amount of at least two light absorbing substances in the blood of a subject, the apparatus comprising:

emitter means for emitting radiation at a minimum of three different wavelengths, detector means for receiving said radiation at each of said wavelengths and producing at least three electrical output signals, signal processing means for processing said output signals and producing a modulation signal for each wavelength, each modulation signal representing pulsating absorption caused by arterialized blood of the subject, transformation means for applying a transformation on each said modulation signal, whereby transformed modulation signals applicable in the Lambert-Beer model are obtained, calculation means, responsive to said transformation means, for determining a value for an invariant on the basis of the transformed modulation signals, the invariant being in the Lambert-Beer model a quotient of two pseudo-isobestic signals, each pseudo-isobestic signal being a weighted sum of two transformed modulation signals, the weighted sum being independent of the relative concentrations of the substances, comparing means, responsive to the calculation means, for determining the difference between said value and a specified value of the invariant, and mapping means for determining an error value based on the difference, the error value indicating a divergence from a specified value of a given quantity.

12. An apparatus according to claim 11, wherein the mapping means includes a look-up table for retrieving the error value corresponding to a given difference.

13. A sensor for collecting measurement data for a pulse oximeter intended for non-invasively determining an amount of at least two light absorbing substances in the blood of a subject, the sensor comprising:

emitter means for emitting radiation at a minimum of three different wavelengths, detector means for receiving said radiation at each of said wavelengths and producing at least three electrical output signals, storage means including a first set of data allowing an apparatus connected to the sensor to determine a value for an invariant which is a quotient of two pseudo-isobestic signals, each pseudo-isobestic signal being a weighted sum of two theoretical measurement signals, the weighted sum being theoretically independent of the relative concentrations of said substances in the blood of the subject.

14. A sensor according to claim 13, wherein the first set of data includes at least one value for the invariant.

15. A sensor according to claim 14, wherein the first set of data includes transformation curves for transforming in-vivo measurement signals for application to the Lambert-Beer model.

16. A sensor according to claim 15, wherein the transformation curves are stored in numeric format.

* * * * *